(12) United States Patent
Park et al.

(10) Patent No.: US 12,233,099 B2
(45) Date of Patent: Feb. 25, 2025

(54) COMPOSITION FOR PROMOTING MYOGENESIS, CONTAINING PROCESSED GINSENG EXTRACT

(71) Applicant: GREEN CROSS WELLBEING CORPORATION, Seongnam-si (KR)

(72) Inventors: Sun Kyu Park, Seongnam-si (KR); Jeom Yong Kim, Seongnam-si (KR); Young Hyo Yoo, Seongnam-si (KR); Min Jung Jang, Seongnam-si (KR); Chang Taek Oh, Seongnam-si (KR); Min Ju Lim, Seongnam-si (KR); Gwan Su Yi, Daejeon (KR); Yi Li, Daejeon (KR); Yoon Hyeok Lee, Seoul (KR); Jae Cheal Yoo, Jinju-si (KR)

(73) Assignee: GREEN CROSS WELLBEING CORPORATION, Seoul (KR)

( * ) Notice: Subject to any disclaimer, the term of this patent is extended or adjusted under 35 U.S.C. 154(b) by 1128 days.

(21) Appl. No.: 17/059,122

(22) PCT Filed: May 24, 2019

(86) PCT No.: PCT/KR2019/006265
§ 371 (c)(1),
(2) Date: Nov. 25, 2020

(87) PCT Pub. No.: WO2019/226015
PCT Pub. Date: Nov. 28, 2019

(65) Prior Publication Data
US 2021/0205387 A1    Jul. 8, 2021

(30) Foreign Application Priority Data

May 25, 2018   (KR) ........................ 10-2018-0059749

(51) Int. Cl.
| | | |
|---|---|---|
| A61K 36/00 | (2006.01) |
| A23L 33/00 | (2016.01) |
| A23L 33/105 | (2016.01) |
| A61K 9/00 | (2006.01) |
| A61K 31/704 | (2006.01) |
| A61K 36/258 | (2006.01) |
| A61P 21/00 | (2006.01) |

(52) U.S. Cl.
CPC .......... *A61K 36/258* (2013.01); *A23L 33/105* (2016.08); *A23L 33/40* (2016.08); *A61K 9/0056* (2013.01); *A61K 31/704* (2013.01); *A61P 21/00* (2018.01); *A23V 2002/00* (2013.01); *A61K 2236/19* (2013.01); *A61K 2236/51* (2013.01)

(58) Field of Classification Search
CPC .................................................. A61K 36/258
See application file for complete search history.

(56) References Cited

U.S. PATENT DOCUMENTS

| 9,512,453 B2 | 12/2016 | Yoo et al. |
| 2016/0213723 A1 | 7/2016 | Yoo et al. |
| 2017/0260275 A1 | 9/2017 | Kortebein et al. |

FOREIGN PATENT DOCUMENTS

| CN | 103724391 A | * | 4/2014 |
| JP | 2008 179620 A | | 8/2008 |
| JP | 2017 149749 A | | 8/2017 |
| KR | 10-0992800 B1 | | 11/2010 |
| KR | 10-1595426 B1 | | 2/2016 |
| KR | 20170001037 A | * | 1/2017 |
| KR | 10-2017-0058035 A | | 5/2017 |
| KR | 10-1771486 B1 | | 8/2017 |
| KR | 2017-0094292 A | | 8/2017 |
| KR | 10-1966117 B1 | | 4/2019 |

OTHER PUBLICATIONS

Meng Sijin, Advances in Molecular Biology of Skeletal Muscle Cells, pp. 177-178, Wuhan University of Technology Press, Dec. 2010.
Extended European Search Report issued for European Patent Application No. 19 807 637.4 on Jan. 7, 2022, 10 pages.
Go Ga-Yeon et al., Ginsenoside Rg1 from Panax ginseng enhances, myoblast differentiation and myotube growth, Journal of Ginseng Research. 2017;41(4): 608-614.
International Search Report issued for International Application No. PCT/KR2019/006265 on Sep. 3, 2019, 4 pages.
Lee SY, et al., Black ginseng activates Akt signaling, thereby enhancing myoblast differentiation and myotube growth, J Ginseng Res., 2018;42(1):116-121.
Chen CF, et al., Comparison of the pharmacological effects of Panax ginseng and Panax quinquefolium, Acta Pharmacol Sin., 2008;29(9):1103-1108.
Kim HS, et al., Effects of ginsenosides Rg3 and Rh2 on the proliferation of prostate cancer cells, Arch Pharm Res., 2004;27(4):429-435.
Li F, et al., Ginsenoside Rg1 prevents starvation-induced muscle protein degradation via regulation of AKT/mTOR/FoxO signaling in C2C12 myotubes., Exp. Ther. Med., 2017;14(2):1241-1247.
Lobina C, et al. Protective effect of Panax ginseng in cisplatininduced cachexia in rats, Future Oncol., 2014;10(7):1203-1214.

* cited by examiner

*Primary Examiner* — Qiuwen Mi
(74) *Attorney, Agent, or Firm* — ROTHWELL, FIGG, ERNST & MANBECK, P.C.

(57) ABSTRACT

The present invention relates to a composition for promoting myogenesis, containing, as an active ingredient, a processed ginseng extract in which a trace amount of a ginsenoside ingredient is increased. It has been ascertained that the processed ginseng extract promotes the differentiation of myoblasts into muscle and inhibits muscle atrophy caused by myostatin, which is a myogenesis inhibitory factor, and thus it is expected that a composition for preventing or treating muscle disorder-related diseases, having excellent effects, can be developed.

2 Claims, 4 Drawing Sheets

COMPOSITION FOR PROMOTING MYOGENESIS, CONTAINING PROCESSED GINSENG EXTRACT

CROSS-REFERENCE TO RELATED APPLICATION(S)

This application is a 35 U.S.C. 371 National Phase Entry Application from PCT/KR2019/006265 filed on May 24, 2019, designating the United States, which claims the benefits of filing date of Korean Patent Application No. 10-2018-0059749 filed on May 25, 2018, the entire contents of which are incorporated herein by reference.

TECHNICAL FIELD

The present invention relates to a composition for myogenesis promotion containing a processed ginseng extract and, more specifically, to a composition for prevention or treatment of a muscle disease, the composition containing as an active ingredient a processed ginseng extract, of which trace ginsenosides with a myogenesis promoting effect are increased.

BACKGROUND OF THE INVENTION

Muscles are an organ that accounts for the largest part of the human body. It is essential to secure appropriate muscle mass of the human body in maintaining the structure of the human body, allowing each organ of the human body to perform its functions, and preventing a various types of diseases.

Muscles are largely classified into smooth muscles, cardiac muscles, and skeletal muscles. Skeletal muscles account for a significant part of our whole body and promote the movement of the skeleton. These skeletal muscles do not divide, are composed of multinucleated muscle fibers, and are produced during embryonic formation. After embryonic formation, muscles are formed by growth or myogenesis after birth. Myogenesis also occurs when muscles are damaged by frostbite, sprains, bruise, or the like.

During myogenesis, satellite cells are first activated and the activated satellite cells differentiate into myoblasts (Morgan, J. E., et al., 2003). The differentiated myoblasts divide, fuse, and develop into myotubes, and these myotubes gather to form muscle fibers, and the muscle fibers bundle to finally form a muscle.

Myogenesis is regulated by a variety of muscle regulatory factors, such as MyoD, myogenic factor 5 (Myf5), myogenin, and myogenic regulator factor 4 (MRF4). Of these, MyoD initiates the expression of muscle-specific genes, such as myosin heavy chain (MHC) and muscle creatine kinase (MCK), and induces the differentiation of satellite cells into myoblasts. The induction of myogenin expression by MyoD activation is the most important factor in the fusion of myoblasts and is involved in the formation of myotubes (Zanou, N., et al., 2013).

Myokines are active substances that are expressed or synthesized from skeletal muscles in response to muscle contraction, act in an autocrine, paracrine, or endocrine manner, and are known to regulate the functions of muscles as well as other tissues (Pedersen, B. K., et al., 2008). Representative myokines are myostatin (MSTN), interleukin-6 (IL-6), irisin, and the like.

Myostatin, which is a gene that belongs to a transforming growth factor-$\beta$ (TGF-$\beta$) group, is a protein that directly acts on myocytes to inhibit myogenesis and myocyte differentiation (Groussard, C., et al., 2000; and Huh, J. Y., et al., 2014). It has been known from several previous studies that the knock-down or knock-out of the myostatin gene results in muscle hypertrophy and insulin resistance reduction (Groussard, C., et al., 2000; Huh, J. Y., et al., 2014), and during exercise, the expression level of myostatin decreases, resulting in an increase in muscle size (Huh, J. Y., et al., 2012).

In addition, it is known that MyoD, which is a transcription factor essential for the expression of myofibrillar protein important in myogenesis, is degraded to induce myoatrophy by increasing the degradation of mediated proteins via ubiquitin proteasome pathway (UPP) activated by the myostatin (MSTN) activin type II receptor (ActRIIB)-Smad2 pathway.

Some problems occurring during myogenesis, such as differentiation of aged cells or satellite cells into myoblasts or division of myoblasts, may cause several muscle disorders or diseases, such as muscle atrophy, myopathy, muscle injury, muscle dystrophy, sarcopenia, myoneural conductive disease, and nerve injury (Bonaldo, P., et al., 2013; Wagatsuma, A., et al., 2014).

Sarcopenia, which is a muscle disease caused by problems occurring during myogenesis, may develop due to cachexia. Cachexia is a type of chronic wasting complex syndromes and refers to a high degree of general prostration that can appear at the end stage of cancer, tuberculosis, hemophilia, and the like. In particular, cachexia is accompanied by chronic diseases, such as malignant tumors and chronic heart failure, and produces weight loss accompanied by anorexia, muscle mass and body fat loss, inflammatory responses, and the like.

Muscle reduction due to such cachexia appears as a complex syndrome caused by a continuous reduction in skeletal muscle mass and function impairment, and produces an acute muscle mass reduction, unlike aging showing gradual and slow loss of muscle mass and muscle reduction disease due to myogenesis disorder. These differences in physiological characteristics lead to differences in prevention and treatment. Therefore, even if there is a sign of muscle reduction, treatments adequate for respective characteristics of cachexia, aging, and myogenesis disorders are needed according to the cause of the muscle reduction (Ryu Seung-Wan, 2017).

To overcome myogenesis disorders and diseases, methods of myocyte regeneration have been recently reported, and it is known that such myocyte regeneration stimulates satellite cells, existing outside the myocytes, to cause the division of the satellite cells, thereby forming muscle tissue. It has been reported that the regeneration of myocytes can be applied not only to repair of damaged muscles but also to natural muscle loss due to aging (Conboy, I. M., et al., 2003).

In addition, a study has been reported that the expression of MyoD and myogenin, which are important muscle regulatory factors in myogenesis, is reduced in the progression of cancer cachexia (Blackwell, T. A., et al., 2016), and study results have been reported that in cancer or AIDS-induced muscle wasting (cachexia) mouse models, the expression of myogenin and myosin, which are important muscle regulatory factors in myogenesis, is reduced (Ramamoorthy, S., et al., 2009). Since study results have also been reported that the suppression of myostatin affects muscle volume and functions in cancer cachexia-induced mouse models (Smith, R. C., et al., 2013), cachexia treatment is expected to be possible through myogenesis promotion.

Ginsenosides, which are major functional components, are differently named only ginseng saponins among various saponins in the plant system, and at least 150 types of ginsenosides have been found so far (Christensen, L. P., 2009). It has been revealed that ginsenosides have pharmacological effects, such as central nervous inhibition, mental tranquilization, pain relief, memory improvement, liver injury recovery, protein and lipid synthesis stimulation, anti-diabetes, anti-stress, antioxidative active substance production stimulation, immune regulation, platelet aggregation inhibition, and anti-aging actions, as well as anticancer, anti-allergy, anti-inflammation, indicating that ginsenosides show respective different effects depending on the type of ginsenosides.

It has been known that: ginsenosides Rg1 and Rb1 enhance central nervous system activity; ginsenosides Re and Rg1 and panaxans A and B are good for diabetes; ginsenosides Re and Rg1 promote angiogenesis; and ginsenosides Rg3 and Rh2 show anticancer effects (Chen, C. F., et al., 2008; and Kim, H. S., et al., 2004). It has been revealed in recent studies that some ginseng extracts show effects on cachexia, fatigue, or muscular atrophy. It was shown that GINSELECT containing 0.9-1.4% of ginsenoside Rg1 and 1.7-3.0% of ginsenoside Rb1 prevented body weight reduction and motor ability reduction in mice treated with the anticancer tumor cisplatin (Lobina, C., et al., 2014) and ginsenoside Rg1 prevented muscular atrophy caused by famine by inhibiting protein degradation pathways (Li, F., et al., 2017).

Therefore, the present inventors, when investigating myogenesis promoting effects by using ginsenoside components of ginseng, verified that a processed ginseng extract with increased trace ginsenoside components inhibited the myogenesis inhibitor myostatin and promoted myogenesis, and thus completed the present invention.

The prior art, Korean Patent Registration No. 1771486, is directed to a composition for prevention or treatment of sarcopenia, myocardial infarction, and cardiovascular diseases through activation of myocyte proliferation, the composition containing at least one compound selected from the group consisting of 20(R)(S)-ginsenoside Rh2, ginsenoside Rk2, and ginsenoside Rh3, and the above-mentioned prior art is different from the present invention in view of constitution, action mechanism, and applied disease of a composition. In addition, Korean Patent Registration No. 1595426 discloses a composition for treatment of sarcopenia, the composition containing a processed ginseng extract with increased contents of ginsenosides Rh2 and Rg3, but the effects of inhibiting myostatin and promoting myogenesis in the present invention is neither disclosed nor suggested. Korean Patent Publication NO. 2017-0094292 discloses a composition for treatment of sarcopenia, the composition containing a myostatin antagonist, but the myostatin inhibition effect of the processed ginseng extract with increased contents of Rh2 and Rg3 of the present invention is neither disclosed nor suggested.

DETAILED DESCRIPTION OF THE INVENTION

Technical Problem

An aspect of the present invention is to provide a composition for myogenesis promotion containing a processed ginseng extract.

Another aspect of the present invention is to provide a pharmaceutical composition for prevention or treatment of a muscle disease and a health functional food for alleviation of a muscle disease, each containing the composition for myogenesis promotion.

Technical Solution

In accordance with an aspect of the present invention, there is provided a composition for myogenesis promotion containing a processed ginseng extract as an active ingredient.

The processed ginseng extract may be prepared by: (a) seeding Aspergillus niger strain on a medium containing a ginseng powder and bran; (b) culturing the strain in step (a); (c) purifying the culture in step (b) through an ultrafiltration membrane; (d) separating an enzyme from the purification product in step (c); (e) adding the enzyme in step (d) to a ginseng powder, a red ginseng powder, a ginseng extract, or a red ginseng extract; (f) fermenting the product after addition in step (e); (g) separating the fermentation product in step (f); (h) concentrating a supernatant in step (g); (i) reacting the concentration product in step (h) with at least one organic acid selected from the group consisting of acetic acid, lactic acid, citric acid, malic acid, and tartaric acid; and (j) neutralizing, filtering, purifying, concentrating, and drying the reaction product in step (i).

The composition may contain ginsenosides Rh2 and Rg3 each in 0.5-30 wt %.

The composition may promote myotube differentiation.

The composition may inhibit myoatrophy caused by myostatin.

In accordance with another aspect of the present invention, there is provided a pharmaceutical composition for prevention or treatment of a muscle disease, the pharmaceutical composition containing the composition for myogenesis promotion and a pharmaceutically acceptable carrier.

In accordance with still another aspect of the present invention, there is provided a health functional food for alleviation of a muscle disease, the health functional food containing the composition for myogenesis promotion and a sitologically acceptable food supplement additive.

The muscle disease may be selected from the group consisting of muscular atrophy, myopathy, muscular injury, muscular dystrophy, myasthenia, sarcopenia, myoneural conductive disease, dermatomyositis, diabetic amyotrophy, nerve injury, amyotrophic lateral sclerosis (ALS), cachexia, and degenerative muscle diseases.

The cachexia may be caused by acquired immune deficiency syndrome (AIDS), celiac disease, multiple sclerosis, rheumatoid arthritis, chronic heart failure, congestive heart failure, uremia, tuberculosis, Crohn's disease, untreated or severe type 1 diabetes, anorexia nervosa, and hormone deficiency.

Hereinafter, the present invention will be described in detail.

The present invention is directed to a composition for myogenesis promotion containing a processed ginseng extract as an active ingredient.

The processed ginseng extract is a processed ginseng powder or a processed ginseng extract manufactured by the methods of Korean Patent Registration Nos. 0992800 and 1595426, of which trace ginsenosides are increased by producing a saponinase and then using hydrolysis of the produced saponinase and an organic acid.

The processed ginseng extract may be a processed ginseng powder or a processed ginseng extract having increased trace ginsenosides, wherein the processed ginseng powder or the processed ginseng extract may be prepared by: (a) seeding *Aspergillus niger* strain on a medium containing a ginseng powder and bran; (b) culturing the strain in step (a); (c) purifying the culture in step (b) through an ultrafiltration membrane; (d) separating an enzyme from the purification product in step (c); (e) adding the enzyme in step (d) to a ginseng powder, a red ginseng powder, a ginseng extract, or a red ginseng extract; (f) fermenting the product after addition in step (e); (g) separating the fermentation product in step (f); (h) concentrating a supernatant in step (g); (i) reacting the concentration product in step (h) with at least one organic acid selected from the group consisting of acetic acid, lactic acid, citric acid, malic acid, and tartaric acid; and (j) neutralizing, filtering, purifying, concentrating, and drying the reaction product in step (i).

The trace ginsenosides may be ginsenosides having a myogenesis promoting effect, and are preferably ginsenosides Rh2 and Rg3.

The composition for myogenesis promotion contains ginsenosides Rh2 and Rg3, and the composition of mixed ginsenosides Rh2 and Rg3 has an excellent myogenesis promoting effect compared with a composition containing ginsenoside Rh2 or Rg3 alone.

The contents of the ginsenosides Rh2 and Rg3 may be 0.2-30 wt %, preferably 0.5-30 wt %, and more preferably 1-20 wt %.

The "myogenesis" is that satellite cells are activated to differentiate into myoblasts, the myoblasts are fused to form myotubes, the myotubes gather to form muscle fibers, and then the muscle fibers bundle to finally form a muscle. Various muscle regulatory factors, such as MyoD, myogenic factor 5 (Myf5), myogenin, and muscle regulatory factor 4 (MRF4), and muscle-specific factors, such as myosin heavy chain (MHC) and muscle creatine kinase (MCK), are involved in myogenesis.

The composition for myogenesis promotion can promote the differentiation of myoblasts into myotubes and can increase the breadth of myotubes.

The composition for myogenesis promotion can inhibit myotube atrophy.

The composition for myogenesis promotion can increase the expression of muscle regulatory factors, such as MyoD.

The composition for myogenesis promotion can inhibit myostatin.

The "myostatin" is a protein that acts directly on myocytes to inhibit myogenesis and myocyte differentiation. Myostatin is known to be overexpressed in various diseases, such as aging, muscular dystrophy, amyotrophic lateral sclerosis, chronic heart failure, AIDS, cancer cachexia, renal failure, uremia, and rheumatoid arthritis.

Furthermore, the present invention is directed to a pharmaceutical composition for prevention or treatment of a muscle disease, the pharmaceutical composition containing the composition for myogenesis promotion as an active ingredient.

The pharmaceutical composition can be used to prevent or treat a muscle disease by promoting the differentiation into myocytes.

The pharmaceutical composition of the present invention can prevent or treat a muscle disease by inhibiting myostatin. Preferably, the pharmaceutical composition prevents or treats a muscle disease by inhibiting myoatrophy caused by myostatin.

The muscle disease is a disease that may be caused by deficiency or abnormal reduction of myocytes or dysfunction of myocytes. Preferably, the muscle disease is caused by deficiency or abnormal reduction of myocytes.

The muscle disease may be muscular atrophy, myopathy, muscular injury, muscular dystrophy, myasthenia, sarcopenia, myoneural conductive disease, dermatomyositis, diabetic amyotrophy, nerve injury, amyotrophic lateral sclerosis (ALS), cachexia, degenerative muscle diseases, or the like, but is not limited thereto.

The cachexia is also called wasting syndrome, and is characterized by weight loss accompanied by a lack of appetite, reductions of muscle mass and body fat, inflammatory responses, and the like. The cachexia may be caused by cancer, acquired immune deficiency syndrome (AIDS), celiac disease, multiple sclerosis, rheumatoid arthritis, chronic heart failure, congestive heart failure, uremia, tuberculosis, Crohn's disease, untreated or serious type 1 diabetes, anorexia nervosa, hormone deficiency, or the like, but is not limited thereto. Preferably, the cachexia may be caused by acquired immune deficiency syndrome (AIDS), celiac disease, multiple sclerosis, rheumatoid arthritis, chronic heart failure, congestive heart failure, uremia, tuberculosis, Crohn's disease, untreated or severe type 1 diabetes, anorexia nervosa, and hormone deficiency, and more preferably acquired immune deficiency syndrome (AIDS), The degenerative muscle disease indicates the continuous destruction of muscle, and may be Duchenne muscular dystrophy, Becker's muscular dystrophy, Limb-girdle muscular dystrophy, congenital muscular dystrophy, facioscapulohumeral muscular dystrophy, myotonic dystrophy, oculopharyngeal muscular atrophy, distal muscular dystrophy, Emery-Dreifuss muscular dystrophy, or the like.

In the present invention, the myoatrophy may be the continuous maintenance of muscle contraction. In the muscle contraction, an increase in glycogenesis in the muscle can continuously maintain muscle contraction. For example, it was confirmed that glycogen was increased in the muscle of a patient suffering from Duchenne muscular dystrophy, which is one of the degenerative muscle diseases. In addition, glycogen storage disease is a disease by abnormal glycogen metabolism, and the storage of glycogen into the skeletal muscle produces muscle cramp, progressive muscle weakness, and the like.

The pharmaceutical composition may contain the composition for myogenesis promotion and a pharmaceutically acceptable carrier.

The pharmaceutical composition may be formulated in an oral dosage form, such as a powder, granules, a tablet, a capsule, a suspension, an emulsion, a syrup, or an aerosol, and in the form of an external preparation, a suppository, and a sterile injectable solution, according to a conventional method for each form. Examples of a carrier, a vehicle, and a diluent that may be contained in the pharmaceutical composition may include lactose, dextrose, sucrose, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methyl hydroxybenzoate, propyl hydroxybenzoate, talc, magnesium stearate, and a mineral oil. Specifically, the pharmaceutical composition, when made into a preparation, may be prepared using a diluent or a vehicle, such as a filler, an extender, a binder, a wetting agent, a disintegrant, or a surfactant. Examples of a solid preparation for oral administration include a tablet, a pill, a powder, granules, a capsule, and the like. Such solid preparations are prepared by mixing the composition for myogenesis promotion of the present invention with at least one vehicle, for example, starch, calcium carbonate, sucrose or lactose, gelatin, or the like. Also, a lubricant like magnesium stearate or talc may be used in addition to simple vehicles.

A liquid preparation for oral administration corresponds to a suspension, a liquid for internal use, an emulsion, a syrup, or the like, and examples thereof may include not only simple diluents that are frequently used, such as water and liquid paraffin, but also several types of excipients, such as a wetting agent, a sweetener, a flavoring agent, and a preservative. Examples of a preparation for parenteral administration include a sterile aqueous solution, a non-aqueous solvent, a suspension, an emulsion, a lyophilizer, and a suppository. Examples of the non-aqueous solvent and the suspension may include propylene glycol, polyethylene glycol, a vegetable oil like olive oil, an injectable ester like ethyl oleate, and others. Examples of a substrate for the suppository may include Witepsol, Macrogol, Tween-61, cacao butter, laurin butter, glycerogelatin, and others.

The dose of the pharmaceutical composition of the present invention may vary depending on the age, sex, and body weight of a subject to be treated, a particular disease or pathological condition to be treated, the severity of the disease or pathological condition, the route of administration, and the decision of a prescriber. The decision of the dose on the basis of these factors is within the level of a person skilled in the art, and the dose is usually in a range of approximately 0.01-2000 mg/kg/day. More preferably, the dose is 1-500 mg/kg/day. Administration may be carried out once a day or may be divided several times. The above dose ranges are not intended to limit the scope of the present invention in any way.

The pharmaceutical composition of the present invention may be administered to mammals, such as rats, mice, cattle, and humans, through various routes. All moods of administration may be contemplated, for example, administration may be carried out orally, rectally, or by intravenous, intramuscular, subcutaneous, intrauterine, epidural or intracerebroventricular injection, and via application to the skin.

Furthermore, the present invention is directed to a health functional food for alleviation of a muscle disease, the health functional food containing the composition for myogenesis promotion as an active ingredient.

The health functional food is a health functional food for alleviation of a muscle disease, the health functional food containing the composition for myogenesis promotion and a sitologically acceptable food supplement additive.

The health functional food include a form of a tablet, a capsule, a pill, or a liquid preparation, and examples of a food to which the extract of the present invention can be added include various kinds of foods, beverages, gums, teas, vitamin complexes, health functional foods, and others.

Advantageous Effects

The present invention is directed to a composition for myogenesis promotion, the composition containing, as an active ingredient, a processed ginseng extract, of which trace ginsenosides are increased by producing a saponinase and then using a hydrolysate by the produced saponinase and an organic acid, and it was confirmed that the processed ginseng extract promoted the differentiation of myoblasts into muscle and inhibited the myogenesis inhibitor myostatin.

Therefore, it is expected that a composition for prevention or treatment of a muscle disease having excellent effects can be developed using the processed ginseng extract of the present invention.

MODE FOR CARRYING OUT THE INVENTION

Hereinafter, preferable examples of the present invention will be described in detail. However, the present invention is not limited to the examples described herein and can be embodied in many different forms. Rather, these examples are provided so that the present disclosure will be thorough and complete and will fully convey the scope of the disclosure to those skilled in the art.

The processed ginseng extracts of the present invention were manufactured by the methods disclosed in Korean Patent Registration Nos. 0992800 and 1595426.

Comparative Example 1: Preparation of Ginseng Powder 200 g of 6-year-old ginseng was dried under hot air and then pulverized, to give 60 g of a ginseng powder.

Comparative Example 2: Preparation of Ginseng Concentrate

After 200 g of 6-year-old ginseng was dried under hot air, 1 L of 70% ethanol was added thereto, and then the mixture was stirred at 70° C. for 8 hours, followed by extraction, filtration, and concentration, to give 50 g of a ginseng concentrate.

Comparative Example 3: Preparation of Ginseng Concentrate Powder

After 200 g of 6-year-old ginseng was dried under hot air, 1 L of 70% ethanol was added thereto, and then the mixture was stirred at 70° C. for 8 hours, followed by extraction, filtration, concentration, and drying, to give 30 g of a ginseng concentrate powder.

Comparative Example 4: Preparation of Red Ginseng Powder 200 g of 6-year-old ginseng was steamed at 98° C. for 1 hour and then dried, followed by pulverization, to give 40 g of a red ginseng powder.

Comparative Example 5: Preparation of Red Ginseng Concentrate

After 200 g of 6-year-old ginseng was steamed at 98° C. for 1 hour, 1 L of 70% ethanol was added thereto, and the mixture was stirred at 70° C. for 8 hours, followed by extraction, filtration, and concentration, to give 30 g of a ginseng concentrate.

Comparative Example 6: Preparation of Red Ginseng Concentrate Powder

After 200 g of 6-year-old ginseng was steamed at 98° C. for 1 hour, 1 L of 70% ethanol was added thereto, and the mixture was stirred at 70° C. for 8 hours, followed by extraction, filtration, concentration, and drying, to give 25 g of a red ginseng concentrate powder.

Comparative Example 7: Preparation of Ginseng Powder+0.2% Rh2+0.3% Rg3

0.2 g of ginsenoside Rh2 and 0.3 g of ginsenoside Rg3 were mixed with 99.5 g of the ginseng powder of Comparative Example 1.

Comparative Example 8: Preparation of Red Ginseng Powder+0.2% Rh2+0.3% Rg3

0.2 g of ginsenoside Rh2 and 0.3 g of ginsenoside Rg3 were mixed with 99.5 g of the red ginseng powder of Comparative Example 4.

Comparative Example 9: Preparation of Red Ginseng Powder+1% Rh2

1 g of ginsenoside Rh2 was mixed with 99 g of the red ginseng powder of Comparative Example 4.

Comparative Example 10: Preparation of Red Ginseng Powder+1% Rg3

1 g of ginsenoside Rg3 was mixed with 99 g of the red ginseng powder of Comparative Example 4.

Comparative Example 11: Preparation of Red Ginseng Powder+0.5% Rh2+0.5% Rg3

0.5 g of ginsenoside Rh2 and 0.5 g of ginsenoside Rg3 were mixed with 99 g of the red ginseng powder of Comparative Example 4.

Example 1: Preparation of Processed Ginseng Powder Using Ginseng Powder 250 g of a ginseng powder and 750 g of bran were added, and sterilized using a high-pressure steam sterilizer at 121° C. under 1.5 atm. The sterilized medium was mixed with 2 L of sterilized water, and then an *Aspergillus niger* suspension ($5\times10^5$ spores/g of medium weight) was seeded, and cultured at 28° C. for 7 days. Upon completion of culturing, a 0.02 M sodium acetate buffer was added and mixed, and then the resultant medium was filtered. The filtered culture was filtered using an ultrafiltration membrane (100 KDa or higher) and concentrated, to give 60 g of an enzyme liquid. 30 g of the enzyme liquid was added to 200 g of the ginseng powder of Comparative Example 1, followed by culturing at 28° C. for 18 hours, and then ethanol was added to precipitate an enzyme and the supernatant was concentrated. 2 L of purified water was added to 200 g of the concentrated product, and then 250 g of citric acid was added, followed by stirring at 50° C. for 18 hours. Upon completion of the reaction, 70% ethanol was added, followed by filtration and concentration, to give 200 g of a processed ginseng powder.

Example 2: Preparation of Processed Ginseng Concentrate Using Ginseng Concentrate After 250 g of a ginseng powder and 750 g of bran were added, the mixture was sterilized using a high-pressure steam sterilizer at 121° C. under 1.5 atm. The sterilized medium was mixed with 2 L of sterilized water, and then an *Aspergillus niger* suspension ($5\times10^5$ spores/g of medium weight) was seeded, and cultured at 28° C. for 7 days. Upon completion of culturing, a 0.02 M sodium acetate buffer was added and mixed, and then the resultant medium was filtered. The filtered culture was filtered using an ultrafiltration membrane (100 KDa or higher) and concentrated, to give 60 g of an enzyme liquid. 30 g of the enzyme liquid was added to 200 g of the ginseng concentrate of Comparative Example 2, followed by culturing at 28° C. for 18 hours, and then ethanol was added to precipitate an enzyme and the supernatant was concentrated. After 2 L of purified water was added to 200 g of the concentrated product, 250 g of citric acid was added, followed by stirring at 50° C. for 18 hours. Upon completion of the reaction, 70% ethanol was added, followed by filtration and concentration, to give 190 g of a processed ginseng concentrate.

Example 3: Preparation of Processed Ginseng Concentrate Powder Using Ginseng Concentrate Powder After 250 g of a ginseng powder and 750 g of bran were added, the mixture was sterilized using a high-pressure steam sterilizer at 121° C. under 1.5 atm. The sterilized medium was mixed with 2 L of sterilized water, and then an *Aspergillus niger* suspension ($5\times10^5$ spores/g of medium weight) was seeded, and cultured at 28° C. for 7 days. Upon completion of culturing, a 0.02 M sodium acetate buffer was added and mixed, and then the resultant medium was filtered. The filtered culture was filtered using an ultrafiltration membrane (100 KDa or higher) and concentrated, to give 60 g of an enzyme liquid. 30 g of the enzyme liquid was added to 200 g of the powdered ginseng concentrate of Comparative Example 3, followed by culturing at 28° C. for 18 hours, and then ethanol was added to precipitate an enzyme and the supernatant was concentrated. 2 L of purified water was added to 200 g of the concentrated product, and 250 g of acetic acid was added, followed by stirring at 50° C. for 8 hours. Upon completion of the reaction, 70% ethanol was added, followed by filtration, concentration, and drying, to give 195 g of a processed ginseng concentrate powder.

Example 4: Preparation of Processed Red Ginseng Powder Using Red Ginseng Powder After 250 g of a ginseng powder and 750 g of bran were added, the mixture was sterilized using a high-pressure steam sterilizer at 121° C. under 1.5 atm. The sterilized medium was mixed with 2 L of sterilized water, and then an *Aspergillus niger* suspension ($5 \times 10^5$ spores/g of medium weight) was seeded, and cultured at 28° C. for 7 days. Upon completion of culturing, a 0.02 M sodium acetate buffer was added and mixed, and then the resultant medium was filtered. The filtered culture was filtered using an ultrafiltration membrane (100 KDa or higher) and concentrated, to give 60 g of an enzyme liquid. 30 g of the enzyme liquid was added to 200 g of the red ginseng powder of Comparative Example 4, followed by culturing at 28° C. for 18 hours, and then ethanol was added to precipitate an enzyme and the supernatant was concentrated. 2 L of purified water was added to 200 g of the concentrated product, and 250 g of acetic acid was added, followed by stirring at 50° C. for 8 hours. Upon completion of the reaction, 70% ethanol was added, followed by filtration, concentration, and drying, to give 195 g of a processed red ginseng powder.

Example 5: Preparation of Processed Red Ginseng Concentrate Using Red Ginseng Concentrate After 250 g of a ginseng powder and 750 g of bran were added, the mixture was sterilized using a high-pressure steam sterilizer at 121° C. under 1.5 atm. The sterilized medium was mixed with 2 L of sterilized water, and then an *Aspergillus niger* suspension ($5 \times 10^5$ spores/g of medium weight) was seeded, and cultured at 28° C. for 7 days. Upon completion of culturing, a 0.02 M sodium acetate buffer was added and mixed, and then the resultant medium was filtered. The filtered culture was filtered using an ultrafiltration membrane (100 KDa or higher) and concentrated, to give 60 g of an enzyme liquid. 30 g of the enzyme liquid was added to 200 g of the red ginseng concentrate of Comparative Example 5, followed by culturing at 28° C. for 18 hours, and then ethanol was added to precipitate an enzyme and the supernatant was concentrated. 2 L of purified water was added to 200 g of the concentrated product, and 250 g of acetic acid was added, followed by stirring at 50° C. for 18 hours. Upon completion of the reaction, 70% ethanol was added, followed by filtration and concentration, to give 190 g of a processed red ginseng concentrate.

Example 6: Preparation of Processed Red Ginseng Concentrate Powder Using Red Ginseng Concentrate Powder After 250 g of a ginseng powder and 750 g of bran were added, the mixture was sterilized by a high-pressure steam sterilizer at 121° C. under 1.5 atm. The sterilized medium was mixed with 2 L of sterilized water, and then an *Aspergillus niger* suspension ($5 \times 10^5$ spores/g of medium weight) was seeded, and cultured at 28° C. for 7 days. Upon completion of culturing, a 0.02 M sodium acetate buffer was added and mixed, and then the resultant medium was filtered. The filtered culture was filtered using an ultrafiltration membrane (100 KDa or higher) and concentrated, to give 60 g of an enzyme liquid. 30 g of the enzyme liquid was added to 200 g of the red ginseng concentrate of Comparative Example 6, followed by culturing at 28° C. for 18 hours, and then ethanol was added to precipitate an enzyme and the supernatant was concentrated. 2 L of purified water was added to 200 g of the concentrated product, and 250 g of acetic acid was added, followed by stirring at 50° C. for 8 hours. Upon completion of the reaction, 70% ethanol was added, followed by filtration, concentration, and drying, to give 195 g of a processed red ginseng powder.

Table 1 below shows the contents of ginsenosides Rh2 and Rg3 contained in the manufactured products of the examples and the comparative examples of the present invention through analysis by the method disclosed in Korean Patent Registration No. 992800. It was verified that the processed ginseng powders or processed ginseng extracts corresponding to Examples 1 to 6, of which trace ginsenosides are increased by producing a saponinase for a ginseng powder and a red ginseng powder and then using hydrolysis by the produced saponinase and an organic acid, contained large amounts of ginsenosides Rh2 and Rg3, which were increased compared with the ginseng powder and the red ginseng powder, which are target substances of reaction. Comparative Examples 7 to 11 were manufactured for comparison of a myogenesis promoting effect, wherein Comparative Examples 7 to 11 had the same contents of ginsenosides Rh2 and Rg3 as the examples of the present invention by, unlike the examples of the present invention, simply adding ginsenosides Rh2 and Rg3 to a ginseng powder and a red ginseng powder, which were not subjected to hydrolysis by a saponinase and an organic acid.

TABLE 1

Contents of ginsenosides Rg3 and Rh2

| Classification | Content (wt %) | |
|---|---|---|
| | Rh2 | Rg3 |
| Example 1 (Processed ginseng powder) | 0.2 | 0.3 |
| Example 2 (Processed ginseng concentrate) | 3 | 3 |
| Example 3 (Processed ginseng concentrate powder) | 12 | 18 |
| Example 4 (Processed red ginseng powder) | 0.6 | 0.8 |
| Example 5 (Processed red ginseng concentrate) | 1 | 3 |
| Example 6 (Processed red ginseng concentrate powder) | 5 | 10 |
| Comparative Example 1 (ginseng powder) | <0.01 | <0.01 |
| Comparative Example 2 (ginseng concentrate) | <0.5 | <0.5 |
| Comparative Example 3 (ginseng concentrate powder) | <0.5 | <0.01 |
| Comparative Example 4 (red ginseng powder) | <0.01 | <0.01 |
| Comparative Example 5 (red ginseng concentrate) | <0.5 | <0.5 |
| Comparative Example 6 (red ginseng concentrate powder) | <0.01 | <0.01 |
| Comparative Example 7 (99.5 g of ginseng powder + 0.2 g of Rh2 + 0.3 g of Rg3) | 0.2 | 0.3 |
| Comparative Example 8 (99.5 g of red ginseng powder + 0.2 g of Rh2 + 0.3 g of Rg3) | 0.2 | 0.3 |
| Comparative Example 9 (99 g of red ginseng powder + 1 g of Rh2) | 1 | <0.01 |
| Comparative Example 10 (99 g of red ginseng powder + 1 g of Rg3) | <0.01 | 1 |
| Comparative Example 11 (99 g of red ginseng powder + 0.5 g of Rh2 + 0.5 g of Rg3) | 0.5 | 0.5 |

Test Example 1: Animal Cell Culture and Myotube Differentiation Induction

During myogenesis, myoblasts divided and fused to develop into myotubes, finally forming a muscle. Therefore, in order to investigate the effect of the processed ginseng extract of the present invention on myogenesis, the activity to differentiate into myotubes was investigated.

The mouse myoblast C2C12 (C2C12 ATCC CRL-1772) cells were used to investigate the activity to differentiate into myotubes. The C2C12 cells were cultured in a $CO_2$ incubator with 5% $CO_2$ at 37° C., in which Dulbecco's modified eagle's medium (DMEM, Gibco) supplemented with 10% fetal bovine serum (FBS), 100 U/ml penicillin, and 100 U/ml streptomycin were added.

The cultured C2C12 cells were dispensed into a plate, and grown until the cells reached a confluency of approximately 80-90%. The culture was removed, and DMEM containing 2% horse serum (Gibco) was added, followed by culturing, thereby inducing the differentiation into myotubes. Then, the formed myotubes were confirmed through a microscope, and the results are shown in FIG. 1.

Figure 1:
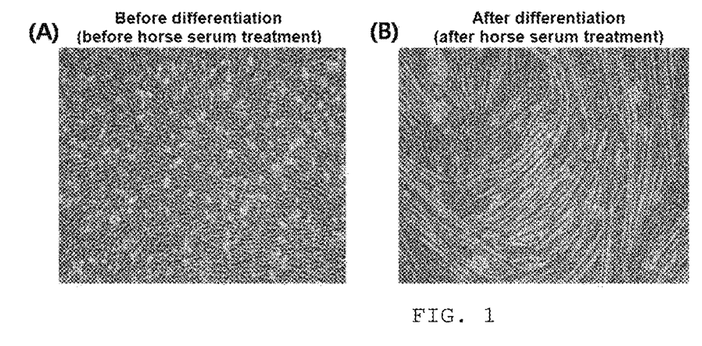
FIG. 1 shows the results of verifying whether the myoblast C2C12 cells differentiate into myotubes.

As shown in FIG. 1, several myoblasts were fused to form tube-shaped myotubes after the induction of differentiation (B), unlike before differentiation (A).

It could be therefore seen that the treatment of C2C12 cells with horse serum could induce myogenesis.

Test Example 2: Verification of Cytotoxicity of Processed Ginseng Extracts

To investigate whether the cytotoxicity of the processed ginseng extract of the present invention, the myotubes obtained from differentiation in Test Example 1 were used.

The myotubes in Test Example 1 were dispensed in a 96-well plate, cultured for 24 hours, treated with the processed ginseng extract of the present invention at 0-100 μg/ml, and then again cultured for 24 hours. After culturing, the intracellular ATP concentrations were measured using Promega's CellTiter-Glo Luminescent cell viability assay kit and a manual provided by the manufacturer, thereby determining cell viability. The results are shown in FIG. 2.

Figure 2:
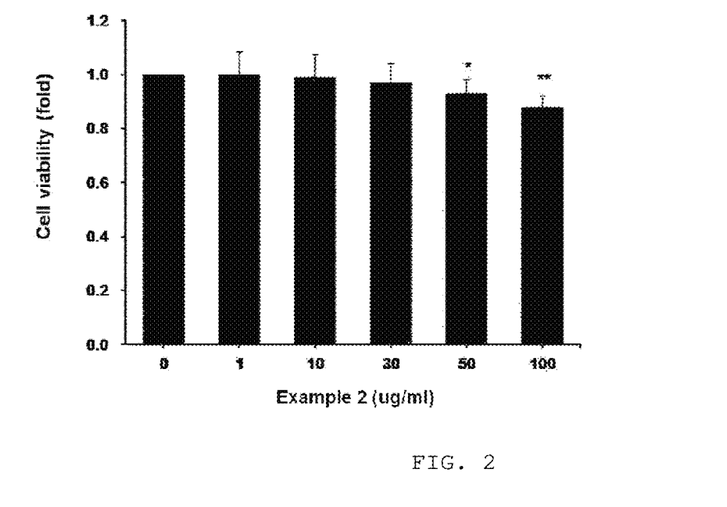
FIG. 2 shows the results of verifying cytotoxicity of a processed ginseng extract of the present invention.

As shown in FIG. 2, regarding the processed ginseng extract of Example 2 among the processed ginseng extracts, the cell viability was slightly reduced up to a concentration of 30 μg/ml, but reduced by about 7-12% at 50 μg/ml and 100 μg/ml compared with normal cells not treated with a processed ginseng extract. That is, it could be predicted that cytotoxicity may be shown when the concentration of the processed ginseng extract of Example 2 was 50 μg/ml or higher.

Similar results could be obtained even in cases of the treatment with the processed ginseng extracts of the other examples.

It could be seen from the above results that the maximum treatment concentration of the processed ginseng extract of the present invention was 30 μg/10.

Test Example 3: Verification of Myotube Formation Promotion by Processed Ginseng Extracts During myogenesis, myoblasts divided and fused to develop into myotubes, finally forming a muscle. Therefore, to investigate the effect of the processed ginseng extract of the present invention on myogenesis, the activity to induce myotube formation was investigated.

A test was conducted by the same method as in the myotube formation induction test in Test Example 1. After the treatment with horse serum, the cells were treated with the processed ginseng extract of Example 2 at 0, 10, and 30 μg/ml, and then cultured for 6 days. On days 0, 2, 4, and 6 of culture, the corresponding cells were fixed, and cell nuclei and cytoplasm were stained by Diff Quick kit (Sysmax, ZS0003, Japan) according to a manual provided by the manufacturer. Then, images were taken using a microscope, and the number of myotubes and the number of cell nuclei were analyzed, and the results are shown in FIG. 3.

Figure 3:
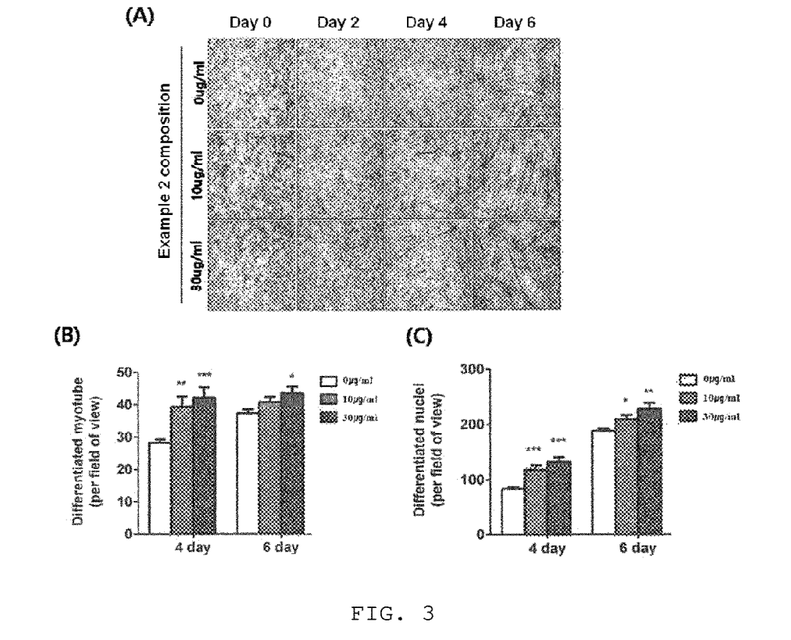
FIG. 3 shows the results of verifying the myotube differentiation effect according to the treatment concentration and time of the processed ginseng extract of the present invention, wherein (A) shows cell images of myotubes; (B) shows the number of differentiated myotubes; and (C) shows the number of nuclei of differentiated myotubes.

As shown in FIG. 3, it was verified through cell images (A), the number of myotubes (B), and the number of cell nuclei (C) that myotubes were increased according to the treatment time and concentration in the treatment with the processed ginseng extract of Example 2.

In addition, the cells were treated with the processed ginseng extracts of Examples 1 to 6 and Comparative Examples 1 to 11 at 10 μg/ml by the same method as in the above test, followed by culturing for 4 days, and then the number of myotubes was analyzed. The results are shown in Table 2 below.

TABLE 2

| Classification | Number of myotubes per field |
|---|---|
| Control (treatment with only horse serum) | 25 |
| Example 1 (Processed ginseng powder) | 31 |
| Example 2 (Processed ginseng concentrate) | 37 |
| Example 3 (Processed ginseng concentrate powder) | 41 |
| Example 4 (Processed red ginseng powder) | 33 |
| Example 5 (Processed red ginseng concentrate) | 34 |
| Example 6 (Processed red ginseng concentrate powder) | 40 |
| Comparative Example 1 (ginseng powder) | 25 |
| Comparative Example 2 (ginseng concentrate) | 26 |
| Comparative Example 3 (ginseng concentrate powder) | 27 |
| Comparative Example 4 (red ginseng powder) | 26 |
| Comparative Example 5 (red ginseng concentrate) | 26 |
| Comparative Example 6 (red ginseng concentrate powder) | 26 |
| Comparative Example 7 (99.5 g of ginseng powder + 0.2 g of Rh2 + 0.3 g of Rg3) | 30 |
| Comparative Example 8 (99.5 g of red ginseng powder + 0.2 g of Rh2 + 0.3 g of Rg3) | 31 |
| Comparative Example 9 (99 g of red ginseng powder + 1 g of Rh2) | 29 |
| Comparative Example 10 (99 g of red ginseng powder + 1 g of Rg3) | 29 |
| Comparative Example 11 (99 g of red ginseng powder + 0.5 g of Rh2 + 0.5 g of Rg3) | 32 |

As can be seen through Table 2 above, the numbers of myotubes in the treatment with the processed ginseng extracts of Comparative Examples 1 to 6 were similar to that in the control group treated with only horse serum, but the number of myotubes was increased in the treatment with the processed ginseng extracts of Examples 1 to 6. In addition, the number of myotubes was increased in the treatment with the processed ginseng extracts of Comparative Examples 7 to 11 in which ginsenosides Rh2 and Rg3 were added alone or together to the ginseng powder and the red ginseng powder of Comparative Examples 1 and 4 rather than the processed ginseng extracts of Comparative Examples 1 and 4, and especially, the number of myotubes was more in the treatment with the processed ginseng extracts of Comparative Examples 7, 8, and 11 in which ginsenosides Rh2 and Rg3 were added together rather than the treatment with the processed ginseng extracts of Comparative Examples 9 and 10 in which ginsenoside Rh2 or Rg3 each was added.

It can be seen from the above results that the co-administration of ginsenosides Rh2 and Rg3, like in the processed ginseng extracts of the present invention, increased a myogenesis promoting effect.

Test Example 4: Verification of Myotube Breadth Increasing Effect by Processed Ginseng Extracts The myotubes formed during myogenesis are increased in length and breadth, and thus are fused with adjacent myotubes to form muscle fibers. Therefore, to investigate the effect of the processed ginseng extract of the present invention on myogenesis, the myotube breadth increasing effect was investigated.

Figure 4:
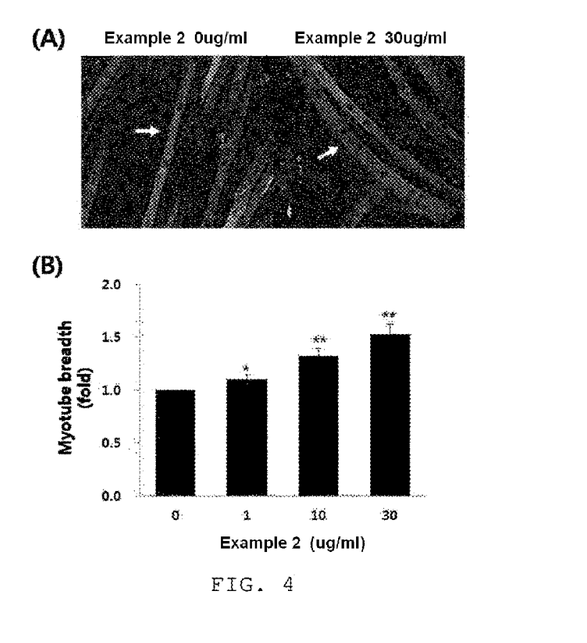
FIG. 4 shows the results of verifying an increase in myotube breath according to the treatment concentration of the processed ginseng extract of the present invention, wherein (A) shows cell images of myotubes and (B) shows the measurement and digitalization results of myotube breadth.

After the C2C12 cells were differentiated into myotubes by the method of Test Example 1, the cells were treated with the processed ginseng extract of Example 2 at 0, 1, 10, and 30 μg/0, followed by culturing for 24 hours. The cultured cells were fixed with 4% paraformaldehyde for 15 minutes, and treated with 0.2% triton X-100 for 15 minutes, and then blocked with 5% bovine serum albumin (BSA) for 6 hours. To observe cell morphology after blocking, an antibody against myosin heavy chain (MHC), which is a myotube forming and maintaining protein, were added, followed by incubation at 4° C. for 12 hours. Then, a secondary antibody conjugated to Alexa Fluor 488 fluorescent substance was incubated at room temperature for 4 hours, followed by immunofluorescent staining. Thereafter, the images of myotubes were observed using the fluorescent substance attached to MHC through a microscope, and the Image J program was used to determine the breadth of myotubes. The results are shown in FIG. 4. As for myotube breadth, the breadths of a total of 100 or more myotubes were measured at random in five regions, and quantified.

As can be seen from the images of myotubes in FIG. 4A and the measurement results of myotube breadth in FIG. 4B, the breadth of myotubes differentiated from C2C12 was increased according to the treatment concentration of the processed ginseng extract of Example 2.

Although not shown herein, it was verified that the treatment with the processed ginseng extracts of Examples 1, 3 to 5 also showed an increase in breadth of myotubes like the treatment with the processed ginseng extract of Example 2.

It can be seen from the above results that the processed ginseng extracts of the present invention had a myogenesis promoting effect by increasing the breadth of myotubes.

Test Example 5: Verification of Myoatrophy Inhibitory Effect of Processed Ginseng Extracts Test Example 5-1: Construction of Myoatrophy Animal Cell Models To investigate the myoatrophy inhibitory effect of the processed ginseng extracts of the present invention, myoatrophy animal cell models were constructed. The animal cell models were constructed on the basis of the fact that the breadth and length of myotubes are reduced in the presence of myoatrophy.

After myotubes were differentiated by the same method as in the induction of myotube differentiation of Test Example 1, the cells were added in DMEM not containing FBS, and cultured for 3 hours. After culturing, the cells were treated with the myogenesis inhibitor myostatin (MSTN) at different concentrations for 24 hours, and the change in breadth of myotubes was measured in order to investigate whether myoatrophy was induced. The change in breadth of myotubes was measured by the same method as in Test Example 4, and after the immunofluorescent staining, images of myotubes were observed using the fluorescent substance attached to MHC through a microscope, and the Image J program was used to determine the breadth of myotubes. The results are shown in FIG. 5.

Figure 5:
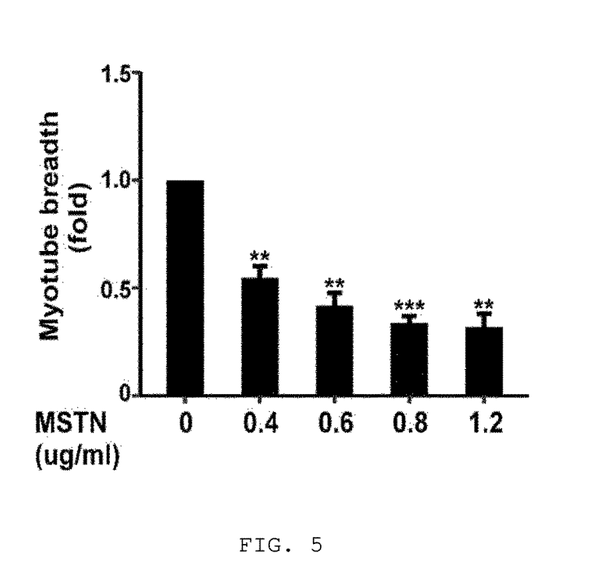
FIG. 5 shows the results of verifying the degree of myotube atrophy according to the treatment concentration of myostatin (MSTN).

As shown in FIG. 5, it was verified that the myotubes treated with myostatin, compared with the myotubes not treated with myostatin, were reduced in breadth of myotubes with the increase of the treatment concentration, and the myotubes treated with 0.4 μg/0 myostatin resulted in a greatest reduction in breadth of myotubes.

Accordingly, the treatment with 0.4 μg/0 myostatin was selected in the construction of myoatrophy animal cell models for investigating the myoatrophy inhibitory effect of the processed ginseng extracts of the present invention.

Figure 6:
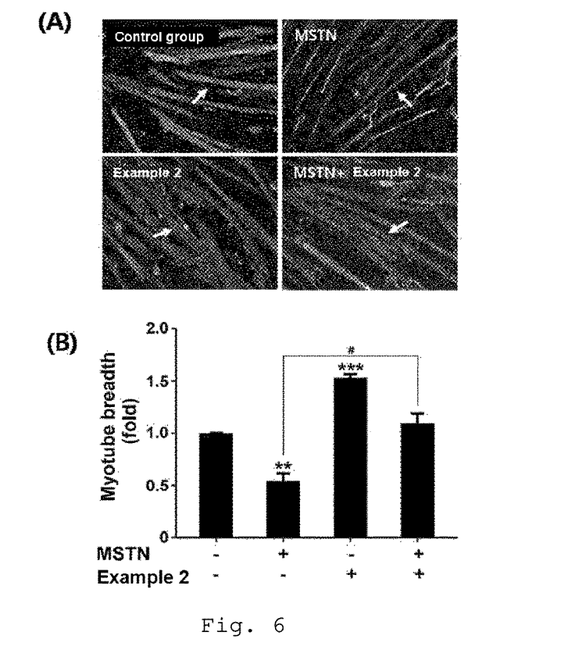
FIG. 6 shows the results of verifying an effect of inhibiting myotube atrophy caused by myostatin through the processed ginseng extract of the present invention, wherein (A) shows cell images of myotubes and (B) shows the measurement and quantification results of myotube breadth.

Test Example 5-2: Verification of Myoatrophy Inhibitory Effect of Processed Ginseng Extracts To investigate the myoatrophy inhibitory effect of the processed ginseng extracts of the present invention, myoatrophy was induced by the same method as the construction method of myoatrophy animal cell models in Test Example 5-1, and then the change in myotube breadth was observed. The results are shown in FIG. 6. The myotubes were treated with 0.4 μg/0 myostatin (MSTN) and 30 μg/0 the processed ginseng extract of Example 2 alone or in combination, and the myotubes not treated with myostatin and the processed ginseng extract of Example 2 were used as a control group.

It can be seen from the images of myotubes in FIG. 6A and the measurement results of myotube breadth in FIG. 6B that the myotube breadth was increased in the treatment with the processed ginseng extract of Example 2 compared with the control group while the myotube breadth was reduced in the treatment with myostatin (MSTN). It was also verified that the myotube breadth reduced by myostatin was increased in the treatment with myostatin and the processed ginseng extract of Example 2 together.

It can be seen from the above results that the processed ginseng extracts of the present invention could increase the myotube breadth and inhibit myoatrophy caused by myostatin during myogenesis.

Test Example 6: Verification of Myostatin-Associated Signaling Inhibitory Effect of Processed Ginseng Extract Test Example 6-1: Verification of Smad2 Phosphorylation Inhibitory Effect Myostatin (MSTN) is known to induce myoatrophy by increasing ubiquitin proteasome pathway (UPP)-mediated protein degradation through activation of the activin type II receptor (ActRIIB)-Smad2 signaling pathway. Therefore, to investigate the inhibitory effect of the processed ginseng extracts of the present invention on myoatrophy caused by myostatin, it was examined whether or not Smad2 phosphorylation was inhibited in the ActRIIB-Smad2 pathway.

The myotubes differentiated by the same method as in Test Example 5-2 were treated with myostatin and the processed ginseng extract of Example 2 to secure cells, and the cells were subjected to Western blotting. The treatment concentrations of the processed ginseng extract of Example 2 was 0, 10, 30, and 100 µg/ml. A lysis buffer was added to the secured cells to lyse cells, and then centrifugation was used to secure proteins of the supernatant. The secured proteins of the supernatant were separated through sodium dodecyl sulfate polyacrylamide gel electrophoresis (SDS-PAGE) and transferred to a polyvinylidene fluoride (PVDF) membrane. The membrane was blocked by a blocking solution, treated with a primary antibody in order to determine the amounts of Smad2 and phosphorylated Smad2 (pSmad2), and then treated with a secondary antibody to the primary antibody. Then, enhanced chemiluminescence (ECL, Amersham) was used to examine protein expression. The protein band density was quantified, and the results are shown in FIG. 7.

Figure 7:
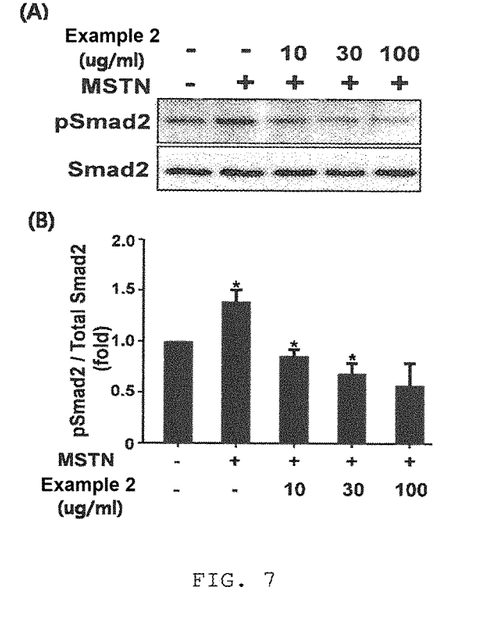
FIG. 7 shows the results of verifying the effect of inhibiting phosphorylation of Smad2, which is a signaling factor associated with myotube atrophy caused by myostatin, in the processed ginseng extract of the present invention, wherein (A) shows expression bands of phosphorylated Smad2 (pSmad2) and (B) shows the results of quantifying density of expression bands.

As can be seen from the protein expression band results in FIG. 7A and the results of quantifying expression levels in FIG. 7B, it was verified that Smad2 phosphorylation (pSmad2) was increased when the myotubes were treated with myostatin (MSTN) while Smad2 phosphorylation (pSmad2) was reduced with the increase of the treatment concentration when the myotubes were treated with the processed ginseng extract of Example 2.

Test Example 6-2: Verification of MyoD Degradation Pathway Inhibitory Effect

It has been known that the degradation of MyoD, a core transcription factor in the expression of myofibrillar proteins important for myogenesis, is driven by the UPP procedure activated via the myostatin (MSTN)-ActRIIB-Smad2 pathway. The UPP procedure is regulated by ubiquitinated E3 ligases specialized to a protein of interest, and MAFbx is known to be the E3 ligase of MyoD, which is a core in this procedure. Therefore, the changes in MyoD and MAFbx contents were examined to investigate the inhibitory effect of the processed ginseng extract of the present invention on myoatrophy caused by myostatin.

The myotubes differentiated by the same method as in Test Example 5-2 were treated with myostatin and the processed ginseng extract of Example 2 to secure cells. The treatment concentrations of the processed ginseng extract of Example 2 was 30 µg/ml. The secured cells were subjected to Western blotting using antibodies corresponding to MyoD and MAFbx by the same method as in Test Example 6-1, and the results are shown in FIG. 8.

Figure 8:
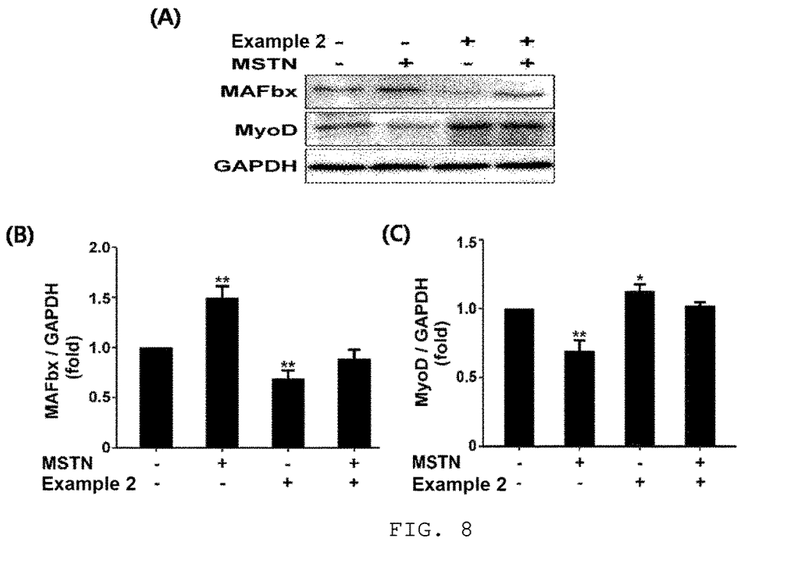
FIG. 8 shows the results of verifying the expression regulatory effects of MoyD, a core transcription factor in the expression of myofibrillar proteins, and MAFbx, an enzyme for degrading MyoD, in the processed ginseng extract of the present invention, wherein (A) shows the bands of confirming the protein expression of MyoD, MAFbx, and GAPDH; (B) shows the results of quantifying the expression of MAFbx compared with GAPDH in the presence or absence of the processed ginseng extract of the present invention; and (C) shows the results of quantifying the expression of MyoD compared with GAPDH in the presence or absence of the processed ginseng extract of the present invention.

As shown in the MAFbx and MyoD protein expression band results in FIG. 8A and the quantification results of MAFbx (FIG. 8B) and MyoD (FIG. 8C) expression levels, the treatment of myotubes with myostatin (MSTN) resulted in an increase in MAFbx expression and a reduction in MyoD expression, while the treatment with the processed ginseng extract of Example 2 resulted in a reduction in MAFbx expression increased by MSTN and an increase in MyoD expression reduced by MSTN.

It can be seen through the results of Test Examples 6-1 and 6-2 that the processed ginseng extracts of the present invention promoted myogenesis by inhibiting signaling of the myogenesis inhibitor myostatin.

The invention claimed is:

1. A method for treating a muscle-atrophy-related disease in a mammal in need thereof, comprising administering to the mammal an extract of processed ginseng, wherein the muscle atrophy-related disease is selected from the group consisting of muscular atrophy, myopathy, muscular injury, muscular dystrophy, myasthenia, myoneural conductive disease, dermatomyositis, diabetic amyotrophy, nerve injury, amyotrophic lateral sclerosis (ALS), cachexia, and degenerative muscle diseases,
   wherein the extract of processed ginseng inhibits myoatrophy caused by myostatin,
   wherein the extract of processed ginseng is prepared by:
   (a) seeding *Aspergillus niger* strain on a medium containing a ginseng powder and bran;
   (b) culturing the strain in step (a);
   (c) purifying the culture in step (b) through an ultrafiltration membrane;
   (d) separating an enzyme from the purification product in step (c);
   (e) adding the enzyme in step (d) to a ginseng powder, a red ginseng powder, a ginseng extract, or a red ginseng extract;
   (f) fermenting the product after addition in step (e);
   (g) separating the fermentation product in step (f);
   (h) concentrating a supernatant in step (g);
   (i) reacting the concentration product in step (h) with at least one organic acid selected from the group consisting of acetic acid, lactic acid, citric acid, malic acid, and tartaric acid; and
   (j) neutralizing, filtering, purifying, concentrating, and drying the reaction product in step (i), and
   wherein the extract of processed ginseng contains ginsenosides Rh2 and Rg3 each in 0.5-30 wt %.

2. The method of claim 1, wherein the cachexia is caused by at least one selected from the group consisting of acquired immune deficiency syndrome (AIDS), celiac disease, multiple sclerosis, rheumatoid arthritis, chronic heart failure, congestive heart failure, uremia, tuberculosis, Crohn's disease, untreated or severe type 1 diabetes, anorexia nervosa, and hormone deficiency.

* * * * *